United States Patent [19]

Dale et al.

[11] Patent Number: 4,919,670
[45] Date of Patent: Apr. 24, 1990

[54] MODULAR HUMERAL PROSTHESIS

[75] Inventors: James L. Dale, Austin; Brain D. Burkinshaw, Pflugerville; Wayne Z. Burkhead, Dallas, all of Tex.

[73] Assignee: Intermedics Orthopedics, Inc., Austin, Tex.

[21] Appl. No.: 151,896

[22] Filed: Feb. 3, 1988

[51] Int. Cl.[5] .............................................. A61F 2/40
[52] U.S. Cl. ...................................... 623/19; 623/22; 623/23
[58] Field of Search .......................... 623/22, 23, 19

[56] References Cited

U.S. PATENT DOCUMENTS

| | | | |
|---|---|---|---|
| 4,004,300 | 1/1977 | English | 623/23 |
| 4,406,023 | 9/1983 | Harris | 623/23 |
| 4,430,761 | 2/1984 | Niederer et al. | 623/23 |
| 4,865,605 | 9/1989 | Dines et al. | 623/19 |

FOREIGN PATENT DOCUMENTS

| | | | |
|---|---|---|---|
| 2015324 | 11/1971 | Fed. Rep. of Germany | 623/23 |
| 2400650 | 7/1974 | Fed. Rep. of Germany | 623/19 |
| 3415934 | 10/1985 | Fed. Rep. of Germany | 623/22 |
| 2567019 | 1/1986 | France | 623/19 |
| 2579454 | 10/1986 | France | 623/19 |
| 1279629 | 12/1986 | U.S.S.R. | 623/19 |

OTHER PUBLICATIONS

Amstutz, H. C., "The Trapezoidal-28 TM Total Hip Replacement," Zimmer (Catalog), p. D11, Mar. 1975.

*Primary Examiner*—Richard J. Apley
*Assistant Examiner*—Stephanie L. Iantorno
*Attorney, Agent, or Firm*—John R. Merkling

[57] ABSTRACT

A modular humeral prosthetic device comprising a humeral stem having a substantially cylindrical distal end for insertion within the medullary canal of a resected human humerus; the stem transforming proximally from the distal end into a widened proximal end being tapered from anterior to posterior aspect; the proximal end having a proximal end surface which is angled relative to the axis of the distal end; a collar extending from the proximal end surface for preventing the stem from subsiding within the medullary canal; a tapered cylindrical mounting lock mechanism disposed on the proximal end surface, the axis of the tapered cylinder being substantially coincident with the central axis of the proximal end surface; a head mechanism having a substantially spherically shaped outer surface for engagement within the glenoid cavity of a human scapula, the outer spherical surface of the head mechanism being less than half the surface of a complete sphere; the head mechanism including a complementary tapered aperture for reversibly receiving the cylindrical lock mechanism in a rigid mechanical coupling engagement; the theoretical center of the spherically shaped head mechanism being disposed at or below the collar.

21 Claims, 1 Drawing Sheet

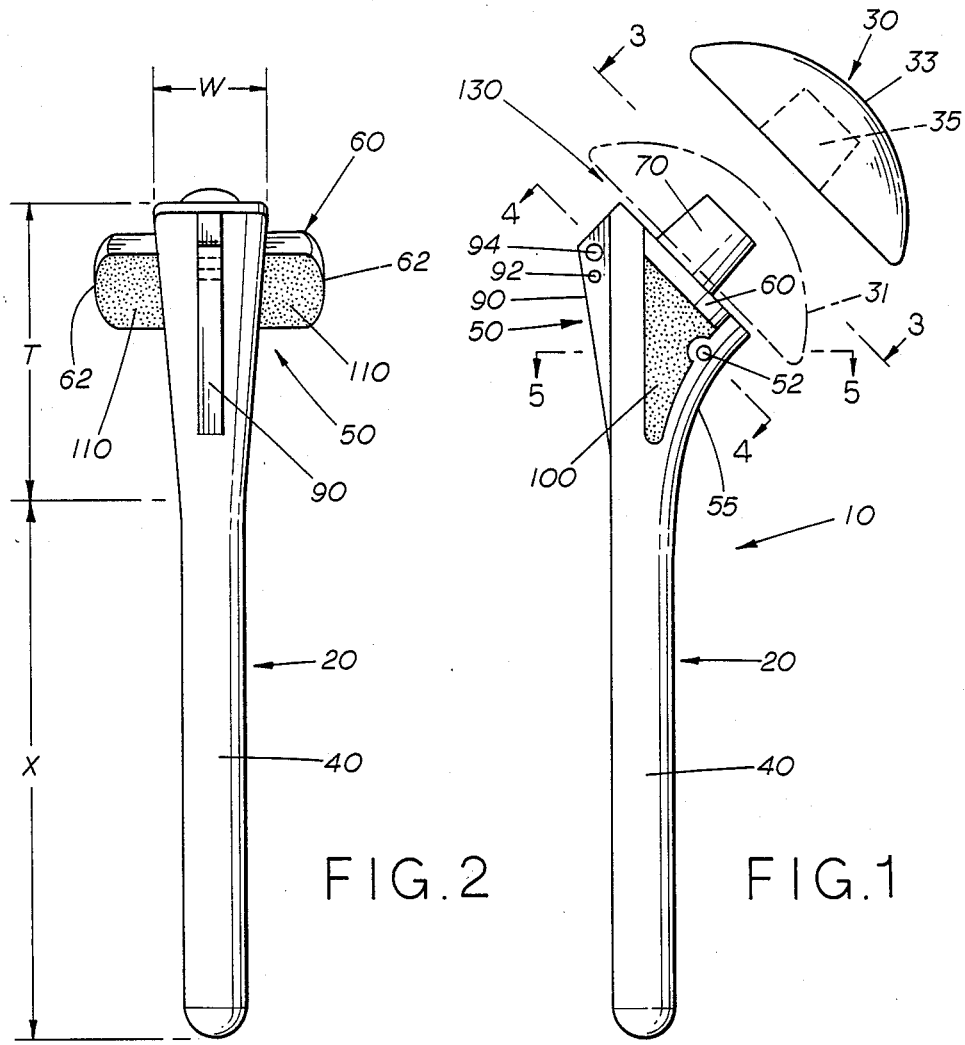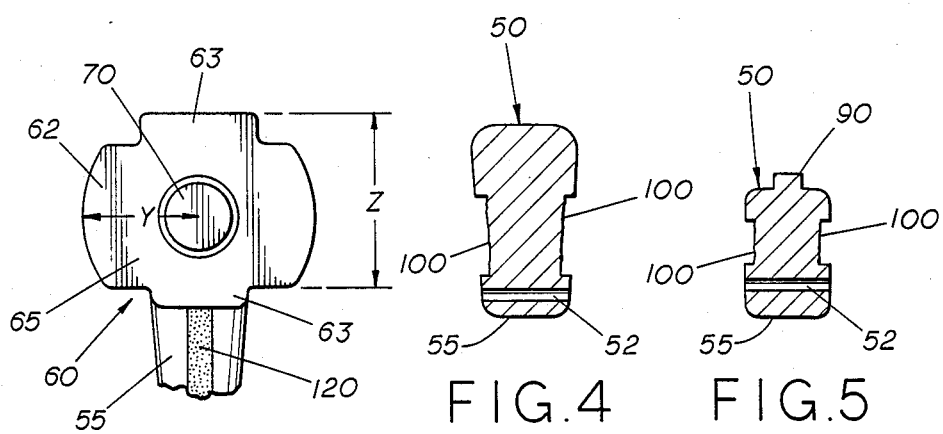

MODULAR HUMERAL PROSTHESIS

BACKGROUND OF THE INVENTION

The present invention relates to prosthetic devices for reconstructing the humerus in human beings, and specifically to a modular humeral prosthetic device comprising stem and head mechanisms readily attachable and detachable to and from each other for allowing intra-operative modification of the device. Prior humeral prosthetic implants have been employed having a stem element for implantation within the medullary canal of a human humerus and a head element for engagement within the glenoid cavity of the human scapula. Such devices do not however achieve true anatomic compatibility with the proximal end of a human humerus and do not provide capability for modification of humeral head size during intraoperative surgery other than by replacement of the entire implant. Although modular devices for implantation in the human femur such as applicants' APR brand hip implant system are known, such implant devices cannot achieve anatomic compatibility with the proximal humeral area and are structurally contradistinct with respect to humeral or scapular tissue attachment or engagement, and load, stress and force distribution and tolerability.

The object of the invention therefore is to provide a modular prosthetic device which is anatomically compatible with the proximal human humerus and scapula and provide the most effective distribution of loads, stresses and forces which are peculiar to the proximal humeral area.

SUMMARY OF THE INVENTION

In accordance with the invention there is provided a modular humeral prosthetic device comprising a humeral stem having a substantially cylindrical distal end for insertion within the medullary canal of a resected human humerus; the stem transforming proximally from the distal end into a widened proximal end being tapered from anterior to posterior aspect i.e. from side to side; the proximal end having a proximal end surface which is angled relative to the axis of the distal end; a collar extending from the proximal end surface for preventing the stem from subsiding within the medullary canal and distributing compressive loading on the proximal end of the humerus, the collar typically having a cloverleaf shape for ease of manufacture of the device as a unitary structure and for avoiding impingement with natural tissue especially on the lateral side of the device; a tapered cylindrical mounting lock mechanism disposed on the proximal end surface, the axis of the tapered cylinder being substantially coincident with the central axis of the proximal end surface; a head mechanism having a substantially spherically shaped outer surface for engagement within the glenoid cavity of a human scapula, the outer spherical surface of the head mechanism being less than half the surface of a complete sphere; the head mechanism including a complementary tapered aperture for reversibly receiving the cylindrical lock mechanism in a rigid mechanical coupling engagement; the theoretical center of the spherically shaped head mechanism being disposed at or below the collar.

The proximal end of the stem also preferably transforms into a trapezoidal shape in cross-section.

The central axis of the proximal end surface is typically disposed at an angle of between about 42 and about 48 degrees relative to the axis of the distal end; and the proximal end of the stem may include a fin protruding from the lateral aspect of the proximal end, the fin gradually increasing in lateral protrusion from distal to proximal end.

The theoretical radius of the spherically shaped head may range from between about 0.5 inches and about 1.5 inches; and the length of the substantially cylindrical end of the stem may range from between about 3.20 inches and about 6.10 inches.

The flattened proximal surface of the collar preferably has a cloverleaf shape; and the underside of the collar preferably includes a porous coating for promoting fixation of natural bone thereto.

A major portion of the anterior and posterior surfaces and the medial radius surface of the trapezoidal end of the stem typically includes a cancellous porous coating for promoting fixation of bone thereto.

The outer spherically shaped surface of the head is preferably polished.

BRIEF DESCRIPTION OF THE DRAWINGS

FIG. 1 is an anterior/posterior directional view of a modular humeral prosthesis according to the invention;

FIG. 2 is a lateral/medial directional view of the prosthesis of FIG. 1 showing the lateral aspect thereof; and, FIG. 3 is a view of the proximal end of the stem portion of the prosthesis of FIG. 1 taken along lines 3—3 of FIG. 1.

FIG. 4 is a cross sectional view of the proximal end of the stem of the device of FIG. 1 taken along lines 4—4 of FIG. 1; and, FIG. 5 is a sectional view of the proximal end of the stem of the device of FIG. 1 taken along lines 5—5 of FIG. 1.

DETAILED DESCRIPTION OF THE INVENTION

Following is a detailed description of a preferred embodiment of the invention.

There is shown in FIG. 1 a modular humeral prosthesis 10 comprising a stem portion 20 and a head portion 30. The stem portion 20 is preferably a unitary structure comprising a metal material such as a cobalt chromium alloy, stainless steel, a titanium alloy such as ASTM F136 Ti6Al-4V ELI or other biocompatible material. The stem 20 is typically configured such that a relatively elongated, substantially cylindrical distal end 40 is provided for insertion within the medullary canal of a human humerus. The distal end 40 preferably transforms, as shown in FIG. 1, into a trapezoidal cross section in the proximal end 50. The length of the distal end 40 preferably ranges in length X, FIG. 2, from between about 3.0 and about 3.6 inches and most preferably from between about 3.20 and about 3.40 inches and ranges in cross-sectional diameter from between about 0.25 and about 0.65 inches, and most preferably from between about 0.25 and about 0.50 inches. The length X of the distal end 40 may in some applications range up to as high as about 6.1 inches, for example in applications where revision surgery is to be performed.

As shown in FIG. 1, the proximal end 50 is generally trapezoidal in cross section, i.e. if a section of the proximal end 50 is taken in a plane which is substantially parallel to the angled end surface 65 of the collar 60 a generally trapezoidal shape will be obtained in such a cross section. FIG. 4 shows a cross section of the proximal end 50 of device 10 of FIG. 1 taken along section lines 4—4 thereof, and, as can be seen from FIG. 4, such a cross-section is generally trapezoidal in shape having rounded corners. By virtue of the trapezoidal configuration of the end 50, any cross section taken about parallel to cross section 4—4 along the distal to proximal length T of end 50 will be generally trapezoidal, the size of such cross sectional trapezoids increasing in size from distal to proximal end by virtue of the taper.

As shown in FIG. 2, the proximal end 50 is tapered from side to side (posterior to anterior aspect), i.e. the taper of end 50 gradually widens in the distal to proximal direction. FIG. 5 shows a section of the proximal end 50 of device 10 of FIG. 1 taken along section lines 5—5 thereof, and, as can be seen from FIG. 5, such a section is generally rectangular in shape having rounded corners. By virtue of the tapered configuration of the end 50, any section taken substantially parallel to section 5—5 along the distal to proximal length T of end 50 will be generally rectangular, the size of such sectional rectangles increasing in size from distal to proximal end. As shown in FIG. 1, the medial arch portion 55 of the proximal end 50 is typically curved as viewed from the direction shown in FIG. 1, but may also be straight. As shown in the angled medial view in FIG. 3, the medial arch section 55 is tapered, i.e. gradually widens in the distal to proximal direction.

The widened proximal end 50 of stem 20 is provided with the generally trapezoidal shape in cross-section and proximally tapered configurations in part to conform to the natural bone anatomy of the proximal medullary canal of a human humerus and in part to provide increased strength to the proximal end 50 such that the wide variety of forces and stresses to which the proximal end of a human humerus are normally subjected may be better tolerated by the prosthesis 10 after implantation.

As best shown in FIGS. 1, 3 the end 50 terminates in a flattened proximal end surface 65 which is positioned such that the central perpendicular axis of the surface 65 forms an angle of preferably between about 42 and about 48 degrees, and most preferably between about 44 and about 46 degrees, relative to the axis of the distal end 40 of the stem 20.

A tapered cylindrically shaped male taperlock 70 protrudes from the surface 65 and is typically integrally formed together with the collar 60 and positioned such that the axis of the male taperlock 70 forms the same angle relative to the axis of the end 40 as the central axis of the surface 65 forms. Most preferably, the male taperlock 70 is positioned such that the taperlock's 70 axis is coincident with the central axis of the surface 65.

A collar 60 protrudes from the edges of the end of the proximal end 50 and typically forms a continuation, on its proximal side, of end surface 65. As shown in FIGS. 1-3 the collar 60 most preferably has a cloverleaf shape with anterior/posterior flare portions 62 which extend outwardly beyond the edges of the tapered anterior/posterior width of the proximal end 50, and lateral/medial portions 63 which preferably extend only so far as to coincide with the ends of the lateral/medial length Z of the proximal end 50. The collar 60 may alternatively be provided with a rounded, oval or other shape but the cloverleaf shaped collar 60 as shown is most preferred insofar as the posterior/anterior sections 62 simultaneously achieves the prevention of subsidence of the stem 20 into the medullary canal of a humerus, the distribution of compressive loading forces around the proximal end of the humerus, and the shortened, non-protruding sections 63 are less likely to cause interference, snagging or the like with surrounding muscle, ligament, bone or other tissue surrounding the proximal end of the humerus after the stem 20 is implanted in a human humerus especially around the lateral aspect thereof. In any event the maximum distance between the outermost edge of a collar and the center of the collar is preferably less than about 0.9 inches. The collar 60 is preferably formed as an integral part of the stem 20 such that the stem 20 including the collar is a unitary structure. The collar 60 may alternatively comprise a separately machined structure which may be attached by conventional means such as by bolting, welding or the like to the most proximal end surface of the trapezoidal end 50. Where the collar 60 comprises a separate structure and is attached to the stem 20, and where the stem 20 and the collar 60 comprise a metal material, the collar is preferably bonded to the end 50 of the stem 20 by treatment at elevated temperature such as diffusion bonding.

As shown in FIGS. 1, 2 the stem 20 is provided with a lateral fin 90 in which one or more apertures such as 92, 94 are typically provided. The lateral fin 90 forms a generally triangular protrusion along the lateral aspect of the proximal end 50 of the stem 20 increasingly protruding from the otherwise straight lateral aspect of the stem 20 from distal end 40 to proximal end 50. The maximum protrusion height of the generally triangular lateral fin 90 typically ranges from between about 0.12 inches and about 0.25 inches. When the stem 20 is properly implanted within a human humerus, for example where the natural head of the humerus has been resected and the distal end 40 properly implanted within the medullary canal, the fin 90 preferably resides in the area posterior of the bicipital groove in the greater tuberosity of the human humerus and may act to prevent rotation of the implanted stem 20 around the axis of the distal end 40 of the stem 20 once implanted. Apertures 92, 94 are typically provided within the fin 90 such that one or more muscles, ligaments or other soft or bony tissue which normally attaches to or around the humeral head or tuberosities such as rotator cuff muscles, the transverse humeral ligament or the like may be attached to the proximal end 50 of the stem 20 by suture insertion through one or more of the apertures 92, 94.

As shown in FIGS. 1-3, the stem 20 is preferably provided with several porous outside surface area portions, such as area 100 on the anterior and posterior aspects of the trapezoidal end 50, area 110 on the underside of the collar 60, and area 120 along the medial arch surface 55 of the stem 20. Such surface areas 100, 110, 120 typically comprise a commercially pure titanium material which preferably has a structure which approximates the structure of natural cancellous bone in order to mimic the abilities of natural cancellous bone to fixate together with new bony matter during natural bone healing and/or growing processes. Such porous material is typically provided on areas such as areas 100, 110 and 120 by providing pocket(s) (not shown) within the otherwise continuous surface of the stem 20 and depositing the porous material therein to fill the pockets (not shown). Other materials useful in promoting bone fixation or healing may be used alone or in combination with the usual titanium material. The typical titanium material which has a structure which approximates the structure of natural cancellous bone is typically referred to as cancellous structured titanium or CSTI.

The stem 20 is preferably implanted within the medullary canal of a human humerus such that the cancellous structured titanium area portions 100, 120 reside within the medullary canal and the coated portion 110 resides on top of the canal thus providing maximum exposure to natural cancellous bone and marrow which surrounds and fills the medullary canal and thus maximizing the potential for fixation of natural bone to areas 100, 110, 120.

One or more additional apertures, such as aperture 52, extending from anterior to posterior aspect are preferably provided immediately adjacent the medial arch 55 of the proximal end 50 for allowing attachment of the end 50 to the proximal end of a humerus by insertion of an appropriate wire, tape, thread or other cord material through the aperture 52 and tying the cord around the proximal end of the natural humerus as when reassembling four part fractures.

The device 10 is provided with a head 30. The outside surface 33 of the head 30 is preferably configured to a substantially spherical contour, the total outside surface area 33 comprising less than half the area of an otherwise complete sphere. The head 30 is implanted such that outside surface 33 is disposed within the glenoid cavity and engages the articulating surface of the glenoid of a human scapula. The surface 33 is polished to a very smooth contour such that any potential snagging of the surface 33 or head 30 with natural human body tissue is minimized and such that the ability of surface 33 to slide within and against the surface of the glenoid cavity in all directions is maximized.

As shown in FIG. 1, the head 30 is provided with an axially central female taperlock aperture 35 which is complementary to the taper of the tapered male protrusion 70. The height of the male taperlock 70 is slightly greater than the height of the female aperture 35 such that when the male 70 and female 35 taperlocks are fully engaged with each other as shown by the phantom lines 31, a small space 130 is left between surface 65 and the underside of head 30. The combined male 70 and female 35 taperlocks comprise a Morse-like taperlock which when engaged serve to lock the head 30 onto the end 50 such that the head 30 will not rotate around protrusion 70. Also, as can be seen from FIG. 1, when the male 70 and female 35 taperlocks are engaged, the theoretical center of the sphere which the head 30 would otherwise form if it were complete, is disposed at or below the collar. Once the male 70 and female 35 taperlocks are engaged with each other rotation of head 30 is prevented and a rigid mechanical coupling is achieved, however, by virtue of the Morse-like taperlock the head 30 may be readily disengaged and removed from protrusion 70 by application of relatively minimal pulling force of head 30 along the axis of protrusion 70.

In a preferred embodiment of the invention the theoretical radius of the spherical head 30 ranges from between about 0.5 inches and about 1.5 inches, most preferably from between about 0.78 and about 1.03 inches, and the maximum distance Y, FIG. 3, between the outermost edge of the collar 60 and the center of the collar is less than about 0.9 inch, most preferably less than about 0.83 inches.

The length Z, FIG. 3, of the long proximal end of the trapezoidal end 50 preferably ranges from between about 0.8 and about 1.7 inches and most preferably ranges from between about 1.0 inches and about 1.5 inches. The axial length T, FIG. 2, along the lateral aspect of the trapezoidal end 50 preferably ranges from between about 1.5 inches and about 2.5 inches and most preferably from between about 1.75 and about 2.13 inches. And, the anterior/posterior width W, FIG. 2, of the trapezoidal end 50 preferably ranges from between about 0.30 inches and about 1.2 inch, and most preferably from between about 0.58 and about 0.92 inches.

The combined geometrical and structural fixtures of the device 10 as described hereinabove thus serve to closely match the natural anatomy of the proximal end of a human humerus and provide a versatile and useful modular prosthetic implant in which the head 30 may be readily removed and replaced, if necessary or desirable, with heads 30 of differing sizes.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A modular humeral prosthetic device comprising:
   a humeral stem having a substantially cylindrical distal end for insertion within the medullary canal of a resected human humerus;
   the stem transforming proximally from the distal end into a widened proximal end being tapered from anterior to posterior aspect;
   the proximal end having a proximal end surface which is angled relative to the axis of the distal end;
   a collar extending from the proximal end surface for preventing the stem from subsiding within the medullary canal;
   a tapered cylindrical mounting lock means disposed on the proximal end surface, the axis of the tapered cylinder being substantially coincident with the central axis of the proximal end surface;
   a head means having a substantially spherically shaped outer surface for engagement within the glenoid cavity of a human scapula, the outer spherical surface of the head means being less than half the surface of a complete sphere,
   the head means including a complementary tapered central aperture for reversibly receiving the cylindrical lock means in a rigid mechanical coupling engagement;
   the theoretical center of the spherically shaped head means being disposed at or below the collar.

2. The device according to claim 1 wherein the central axis of the proximal end surface is disposed at an angle of between about 42 and about 48 degrees relative to the axis of the distal end.

3. The device according to claim 1 wherein the proximal end of the stem includes a fin protruding from the lateral aspect of the proximal end, the fin gradually increasing in lateral protrusion from distal to proximal end.

4. A modular humeral prosthetic device comprising:
   a humeral stem having a substantially cylindrical distal end for insertion within the medullary canal of a resected human humerus;
   the stem transforming proximally from the distal end into a widened proximal end being trapezoidal in cross section;
   the proximal end having a proximal end surface which is angled relative to the axis of the distal end;

a collar extending from the proximal end surface for preventing the stem from subsiding within the medullary canal;

a tapered cylindrical mounting lock means disposed on the proximal end surface, the axis of the tapered cylinder being substantially coincident with the central axis of the proximal end surface;

a head means having a substantially spherically shaped outer surface for engagement within the glenoid cavity of a human scapula, the outer spherical surface of the head means being less than half the surface of a complete sphere;

the head means including a complementary tapered aperture for reversibly receiving the cylindrical lock means in a rigid mechanical coupling engagement;

the theoretical center of the spherically shaped head means being disposed at or below the collar.

5. The device according to claim 4 wherein the central axis of the proximal end surface is disposed at an angle of between about 42 and about 48 degrees relative to the axis of the distal end.

6. The device according to claim 4 wherein the proximal end of the stem includes a fin protruding from the lateral aspect of the proximal end, the fin gradually increasing in lateral protrusion from distal to proximal end.

7. A modular humeral prosthetic device comprising:
a humeral stem having a substantially cylindrical distal end for insertion within the medullary canal of a resected human humerus;

the stem transforming proximally from the distal end into a widened proximal end being tapered from anterior to posterior aspect and trapezoidal in cross section;

the proximal end having a proximal end surface which is angled relative to the axis of the distal end;

a collar extending outwardly from the proximal end surface for preventing the stem from subsiding within the medullary canal;

a tapered cylindrical mounting lock means disposed on the proximal end surface, the axis of the tapered cylinder being substantially coincident with the central axis of the proximal end surface;

a head means having a substantially spherically shaped outer surface for engagement within the glenoid cavity of a human scapula, the outer spherical surface of the head means being less than half the surface of a complete sphere;

the head means including a complementary tapered aperture for reversibly receiving the cylindrical lock means in a rigid mechanical coupling engagement;

the theoretical center of the spherically shaped head means being disposed at or below the collar.

8. The device according to claim 7 wherein the central axis of the proximal end surface is disposed at an angle of between about 42 and about 48 degrees relative to the axis of the distal end.

9. The device according to claim 8 wherein the proximal end of the stem includes a fin protruding from the lateral aspect of the proximal end, the fin gradually increasing in lateral protrusion from distal to proximal end.

10. The device according to claim 8 wherein the theoretical radius of the spherically shaped head means ranges from between about 0.5 inches and about 1.5 inches.

11. The device according to claim 8 wherein the length of the substantially cylindrical end of the stem ranges from between about 3.20 inches and about 6.10 inches.

12. The device according to claim 8 wherein the collar has a cloverleaf shape.

13. The device according to claim 8 wherein the collar includes a porous coating for promoting fixation of natural bone thereto.

14. The device according to claim 8 wherein a major portion of the anterior and posterior surfaces and the medial radius surface of the proximal end of the stem includes a porous coating for promoting fixation of bone thereto.

15. The device according to claim 8 wherein the outer spherically shaped surface of the head is polished.

16. A modular humeral prosthetic device comprising:
a humeral stem having a substantially cylindrical distal end and a widened proximal end;

the proximal end having a proximal end surface which is angled relative to the axis of the distal end;

a male taperlock means protruding from the center of the proximal end surface;

a head means having a substantially spherically shaped outer surface for engagement within the glenoid cavity of a human scapula, the head means including a central female taperlock means for receiving and engaging the male taperlock means in a rigid mechanical coupling engagement;

the outer surface of the spherically shaped head means comprising less than half the surface of a complete sphere, the theoretical center of the spherically shaped head means being disposed at or below the proximal end surface when the male and female taperlocks are lockably engaged.

17. The device according to claim 16 wherein the proximal end has a trapezoidal shape in cross section.

18. The device according to claim 16 wherein the proximal end has a tapered shape in the anterior to posterior direction.

19. The device according to claim 16 wherein the proximal end includes a collar extending outwardly from the proximal end surface.

20. A modular humeral prosthetic device comprising:
A humeral stem having a substantially cylindrical distal end and a widened proximal end;

the proximal end having an end surface disposed at an angle of between 42 and about 48 degrees relative to the axis of the distal end;

and male taperlock means protruding from the center of the proximal end surface;

a head means having an outer surface comprising a substantially spherical shape having less than half the surface of a complete sphere, the outer surface for engagement within the glenoid cavity of a human scapula, the head means including a central female taperlock means for receiving and engaging the male taperlock means in a rigid mechanical coupling engagement.

21. The device according to claim 20 wherein the theoretical center of the spherically shaped head means is disposed at or below the proximal end surface when the male and female taperlocks are lockably engaged.

* * * * *